United States Patent
Orme

(10) Patent No.: US 8,518,409 B2
(45) Date of Patent: Aug. 27, 2013

(54) SYSTEM FOR SELECTIVE CELL TREATMENT USING IDEOTYPICALLY MODULATED PHARMACOEFFECTORS

(75) Inventor: Jacob Orme, Coppell, TX (US)

(73) Assignee: Imperium Biotechnologies, Inc., Coppell, TX (US)

( * ) Notice: Subject to any disclaimer, the term of this patent is extended or adjusted under 35 U.S.C. 154(b) by 106 days.

(21) Appl. No.: 13/116,747

(22) Filed: May 26, 2011

(65) Prior Publication Data

US 2011/0293639 A1 Dec. 1, 2011

Related U.S. Application Data

(63) Continuation-in-part of application No. 12/790,931, filed on May 31, 2010, now Pat. No. 8,383,405.

(51) Int. Cl.
*A61K 39/00* (2006.01)
*A61K 38/54* (2006.01)
*A61K 48/00* (2006.01)
*C12Q 1/68* (2006.01)
*C12N 5/00* (2006.01)
*C12N 5/02* (2006.01)

(52) U.S. Cl.
USPC .................. 424/178.1; 424/94.3; 424/183.1; 435/6.1; 435/375; 514/44 R

(58) Field of Classification Search
None
See application file for complete search history.

(56) References Cited

U.S. PATENT DOCUMENTS

| | | |
|---|---|---|
| 4,724,232 A | 2/1988 | Rideout et al. |
| 4,861,707 A | 8/1989 | Ivanoff et al. |
| 4,867,973 A | 9/1989 | Goers et al. |
| 5,846,565 A | 12/1998 | Brem et al. |
| 2004/0009167 A1 | 1/2004 | Rider |
| 2005/0267061 A1 | 12/2005 | Martin |
| 2010/0323001 A1 | 12/2010 | Pachuk |

OTHER PUBLICATIONS

Notification of Transmittal of the International Search Report and the Written Opinion of the International Searching Authority, or the Declaration dated Jan. 9, 2012 in connection with International Patent Application No. PCT/US11/38393.
Yang Chao, et al., "Engineering a Dimeric Caspase-9: A Re-evaluation of the Induced Proximity Model for Caspase Activation", PLoS Biology, vol. 3, Issue 6, Jun. 2005, p. 1079-1087.
Office Action dated Mar. 13, 2012 in connection with U.S. Appl. No. 12/790,931.

*Primary Examiner* — Robert Landsman

(57) ABSTRACT

In a method embodiment, a method includes introducing a plurality of Ideotypically Modulated Pharmacoeffectors (IMP) into a population of cells. Each IMP may include a detection domain and an activation domain. One or more epitopes is bound by the detection domain. The activation domain is activated in response to the binding. Applications may include but are not limited to viral infections, other intracellular infections, cancers, vector-borne diseases, autoimmune diseases, cellular diseases, cellular enhancement, and research.

15 Claims, 3 Drawing Sheets

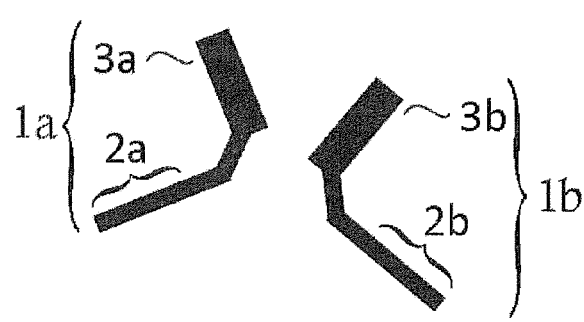
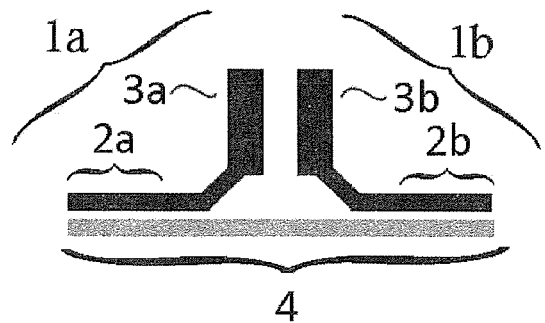
FIG. 3A
FIG. 3B
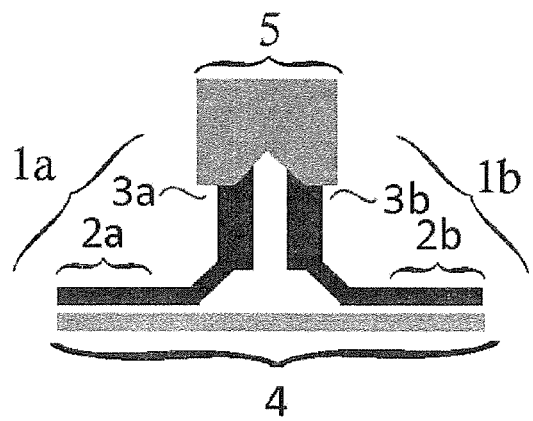
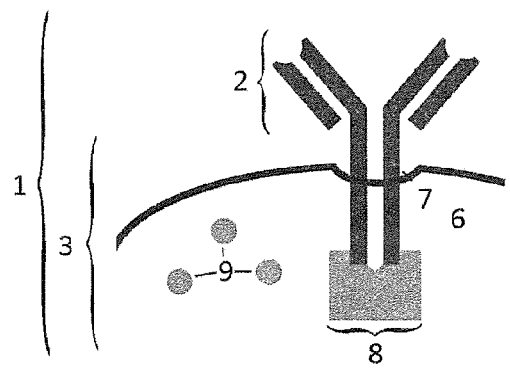
FIG. 3C
FIG. 4
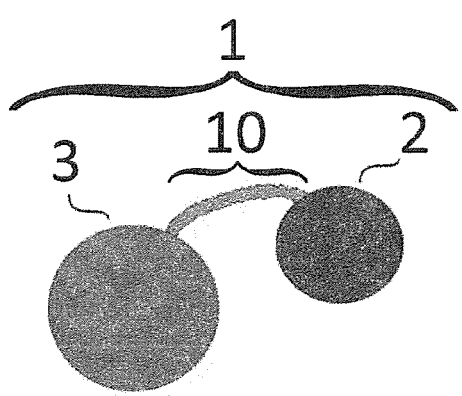
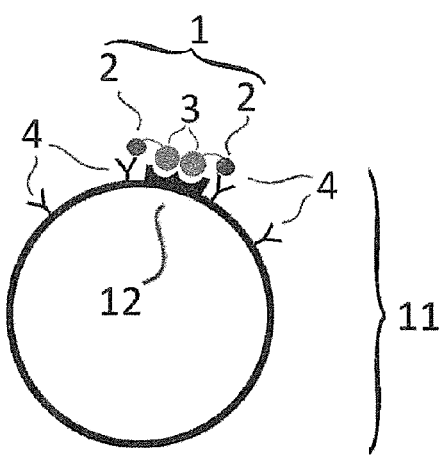
FIG. 5
FIG. 6

US 8,518,409 B2

SYSTEM FOR SELECTIVE CELL TREATMENT USING IDEOTYPICALLY MODULATED PHARMACOEFFECTORS

CROSS-REFERENCE TO RELATED APPLICATION(S) AND CLAIM OF PRIORITY

This application is a continuation-in-part of U.S. application Ser. No. 12/790,931, (now U.S. Pat. No. 8,383,405) entitled IDEOTYPICALLY MODULATED PHARMACO-EFFECTORS FOR SELECTIVE CELL TREATMENT, which was filed on May 31, 2010 and issued on Feb. 26, 2013.

TECHNICAL FIELD OF THE INVENTION

This invention is related generally to ideotype-specific treatments of cells and organisms, and more particularly to ideotype-specific treatments of cells and organisms using engineered Ideotypically Modulated Pharmacoeffectors (IMPs).

BACKGROUND

In the human body, each cell type expresses a unique assortment of proteins, lipids, sugars, nucleotide sequences, and other metabolites. Each of these is a potential antigen, having epitopes with which a molecule having predetermined affinity can interact. The expression of said antigens is modified by the status of the cell and by its environment. This expression becomes further modified when viruses or intracellular bacteria introduce foreign materials into the cell as they infect. Viruses in particular hijack the cell machinery and produce many virion copies that bud off from the cell and infect other cells.

When a person becomes infected by a virus, the immune system has various mechanisms that attempt to detect and destroy infected cells. Unfortunately, many viruses have adapted mechanisms to evade this protection and send duplicated virions to infect other cells. These adaptations succeed because the viruses have two important features: speedy replication and rapid mutation rates. Similar attributes are also characteristic of cancers, weaponized biological agents, and other infections.

SUMMARY

In a method embodiment, a method includes introducing a plurality of engineered Ideotypically Modulated Pharmacoeffectors (IMPs) into a population of cells. Each IMP may include a detection domain and an activation domain. One or more epitopes is bound by the detection domain. The activation domain is activated in response to the binding.

In a system embodiment, each of a plurality of Ideotypically Modulated Pharmacoeffectors include a detection domain and an activation domain. The detection domain has affinity for an epitope. The activation domain is configured such when it is activated, it will cause a downstream effect in a population of cells.

In another system embodiment, there are instructions for the manufacture of a plurality of Ideotypically Modulated Pharmacoeffectors. Each of the plurality of Ideotypically Modulated Pharmacoeffectors includes a detection domain and an activation domain. The detection domain of each IMP of a subset of the plurality of manufactured IMPs is configured to bind to one or more epitopes. The activation domain of each IMP of the subset of the plurality of manufactured IMPs is configured to activate and cause a downstream effect in a population of cells.

Certain embodiments of the method may have a number of technical advantages. For example, some embodiments may be capable of terminating diseased or disease-causing cells. Some other embodiments may include enhancing cells. Some further embodiments may be capable of eliminating carriers of zoonotic diseases. Still other embodiments may reduce complications associated with transplants. Various embodiments may include some, all, or none of the above advantages. Particular embodiments may include other advantages.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 3A shows one example of multiple unbound Ideotypically Modulated Pharmacoeffectors that may be introduced into a population of cells according to one embodiment;

FIG. 3B shows one example of binding of multiple adjacent ideotypical epitopes to the detection domains of multiple Ideotypically Modulated Pharmacoeffectors according to one embodiment;

FIG. 3C shows the interaction of multimerized Ideotypically Modulated Pharmacoeffectors with endogenous cascade mediators according to one embodiment;

FIG. 4 shows an antibody or antibody-like complex capable of blocking the pore of a polymer pouch containing a number of effector molecules according to one embodiment;

FIG. 5 shows a detection domain linked to an activation domain by a linker according to one embodiment;

FIG. 6 shows the binding of a plurality of Ideotypically Modulated Pharmacoeffectors to the surface antigen receptors of ideotypical disease-causing B cells according to one embodiment;

DESCRIPTION OF EXAMPLE EMBODIMENTS

FIGS. 1 through 8B, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged configuration. The invention may, however, be embodied in many different forms and should not be construed as limited to the embodiments set forth herein. Rather, the disclosed embodiments are provided such that this disclosure will be thorough and complete, and will convey the scope of the invention to those skilled in the art. The principles and features of the invention may be employed in varied and numerous embodiments without departing from the scope of the invention.

Figure 1:
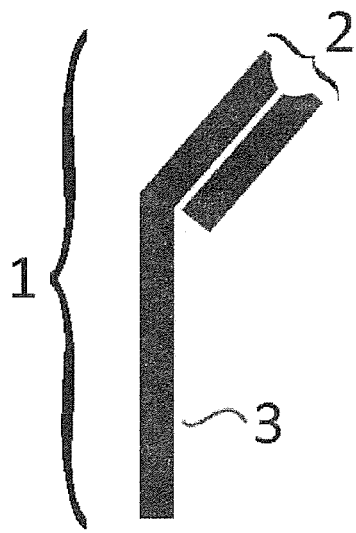
FIG. 1 shows one example of an engineered Ideotypically Modulated Pharmacoeffector including a detection domain and an activation domain according to one embodiment.

FIG. 1 shows one example of an engineered Ideotypically Modulated Pharmacoeffector (1) according to one embodiment. In the illustrated example, an IMP (1) includes a detection domain (2) and an activation domain (3). The term "detection domain" as used herein refers to any molecule (e.g. protein, nucleotide sequence, lipid) that has affinity for a molecule of interest. The term "activation domain" as used herein refers to any molecule (e.g. protein, nucleotide sequence, substance) that may be activated to interact with the cell or its environment in response to the binding of the detection domain. In certain embodiments, "engineered" Ideotypically Modulated Pharmacoeffectors or IMPs (1) may refer to a nonnaturally occurring manufacture or composition of biological matter having a distinctive use. In yet other embodiments, IMPs or IMP-producing substances (e.g. nucleotides) may be introduced into the body for the production of their parts; for instance, a plasmid encoding IMPs may be introduced. Various embodiments are described below.

Figure 2A:
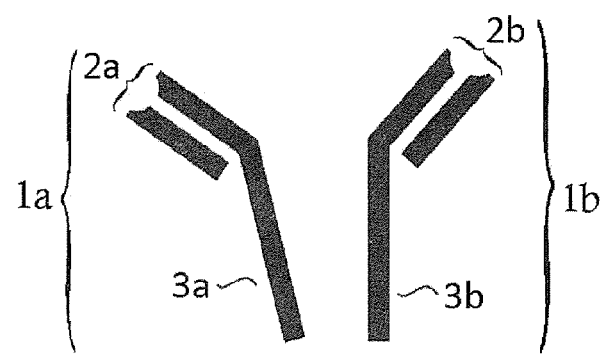
FIG. 2A shows one example of multiple unbound Ideotypically Modulated Pharmacoeffectors that may be introduced into a population of cells according to one embodiment.
Figure 2B:
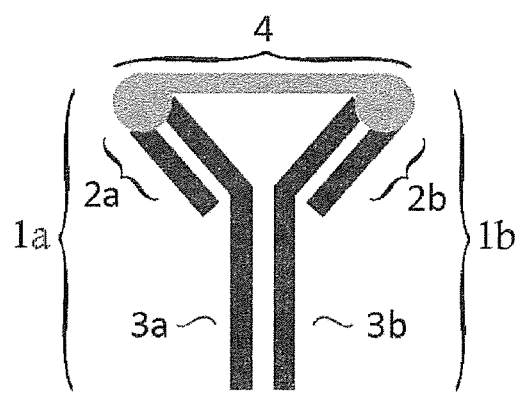
FIG. 2B shows one example of binding of multiple adjacent ideotypical epitopes to the detection domains of multiple Ideotypically Modulated Pharmacoeffectors according to one embodiment.

FIG. 2A shows one example of multiple unbound Ideotypically Modulated Pharmacoeffectors (1a, 1b) that may be introduced into a population of cells according to one embodiment. The detection domains (2a, 2b) of these IMPs (1a,1b) have affinity for adjacent epitopes on a predetermined target antigen (4) when present in the cell of a particular ideotype. The term "epitope" as used herein refers to any part of a molecule of interest with which a detection domain, as defined above, interacts or binds. The terms "ideotype," "ideotypical," and "ideotypically" as used herein refer to the uniqueness or differential expression of the set of antigens (and their concomitant epitopes) expressed in or on a subset of cells. The term "antigen" as used herein refers to any molecule of interest with epitopes. The detection domains (2a,2b) may be identical or different, depending on the application. For instance, in detecting antigens (4) with repetitive epitopes, identical detection domains (2a,2b) may be advantageous. The binding of more than one Ideotypically Modulated Pharmacoeffector (1a,1b) to adjacent epitopes results in the dimerization or multimerization of the activation domains (3a,3b) as shown in FIG. 2B. The terms "dimerization" and "multimerization" as used herein refer to the colocalization of molecules, whether homologous or heterologous, changing the activity of said molecules. As with the detection domains, activation domains may be identical or different, depending on the application. For instance, an activation domain (3a,3b) for inducing cell death may be inactive Caspase-9 monomer, which—when dimerized—converts itself to an active form. In this case, an identical activation domain may be advantageous.

Figure 2C:
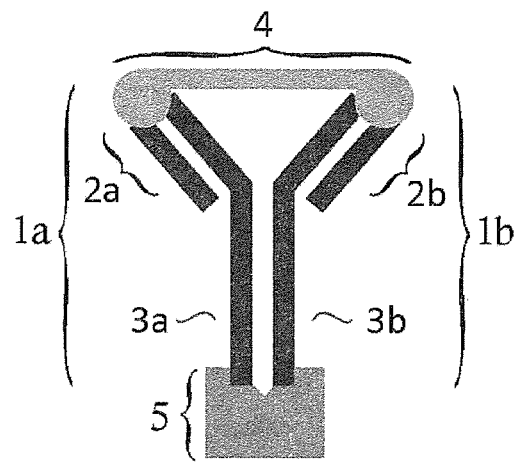
FIG. 2C shows the interaction of multimerized Ideotypically Modulated Pharmacoeffectors with endogenous cascade mediators according to one embodiment.

FIG. 2C shows the interaction of multimerized Ideotypically Modulated Pharmacoeffectors with endogenous cascade mediators (5) from a cell according to one embodiment. This induces a cascade of desired downstream effects in cells which contain the epitopes of the antigen of interest (4). The term "downstream effects" as used herein may refer to any biological result of the interaction of activation domains (3a, 3b) with endogenous molecules (5). In certain circumstances, the epitopes of the antigen of interest (4) may be expressed in a desired target cell type (i.e. ideotype), whether viral, cancerous, or otherwise of interest. As a result, these downstream effects may be induced in these target cells, conferring specificity of downstream effects. In some embodiments, a linker of some sort (e.g. collagen) may conjugate the detection and activation domains as pictured in FIG. 5. The length of this linker may be adjusted to maximize downstream effect.

There are a number of methods by which Ideotypically Modulated Pharmacoeffectors (1) may be manufactured. In one instance, a FAb antibody fragment with specific affinity for the target epitopes may be covalently conjugated to an effector domain by a collagen linker by synthetic conjugating processes. In other instances, an aminophosphonate group may chemically connect the C terminus of a FAb fragment with the N terminus of an inactive Caspase. In another instance, the genetic code for the entire complex may be introduced in a bacterial, human, or other organic species that may mass-produce the complex as a unit or as subunits to be conjugated later. In still another instance, an anti-sense nucleotide sequence specific for target epitopes of nucleotide sequences (2a, 2b) in the cell could be chemically conjugated to an activation domain (3a, 3b). This may be accomplished through carbodiimides or other available means of conjugation. As a non-limiting examples, in one instance, a nucleotide detection domain (2a,2b) contains an azide that may be linked via Staudinger ligation chemistry to activated ester groups on an activation domain (3a,3b). In another instance, a nucleotide detection domain (2a, 2b) may contain a benzaldehyde group that may be linked via modified Pictet-Spengler ligation in glacial acetic acid to terminal histidine residues on an activation domain (3a,3b). Both of the aforementioned ligation methods have been used to produce working prototypes by the applicant of the present disclosure. In yet other instances, other ligation methods may be utilized. These instances are only some of the ways in which the embodiment could be manufactured and should not be considered limiting. Further examples of manufacturing of IMPs are described below with reference to FIGS. 2A-6.

FIG. 3A shows one example of multiple unbound Ideotypically Modulated Pharmacoeffectors (1a,1b) that may be introduced into a population of cells according to one embodiment. In this embodiment, detection domains (2a,2b) may comprise antisense nucleotide strands. The terms "antisense" and "complementary" as used herein refer to nucleotide sequences of any length with coded affinity for another nucleotide strand; as a non-limiting example, the sequence 5'-ATGCC-3' could be complementary or antisense to the sequence 5'-GGCAT-3'. In some embodiments, activation domains (3a,3b) may perform substantially the same functions as the activation domain shown in FIGS. 1-2C. These elements may be conjugated (2a,3a and 2b,3b) to form an IMP (1a, 1b) by carbodiimides or by some other functional group or linker in a chemical process.

FIG. 3B shows one example of binding of multiple adjacent ideotypical epitopes (4) to the detection domains (2a,2b) of multiple Ideotypically Modulated Pharmacoeffectors according to one embodiment. In this embodiment that may use dimerization or multimerization methods, epitopes (4) may comprise nucleotide strands that may be unique to target cells of interest. In one embodiment, for instance, these strands may comprise a nucleotide sequence introduced by a virus as it infects a cell. In such a case, the detection domains (2a,2b) may be antisense nucleotide sequences that are complementary to that introduced by the virus.

FIG. 3C shows the interaction of multimerized Ideotypically Modulated Pharmacoeffectors (1a,1b) with endogenous cascade mediators (5) according to one embodiment. In certain circumstances, the nucleotide epitope (4) may be expressed in a particular target cell type (i.e. ideotype), whether viral, cancerous, or otherwise of interest. In certain other circumstances, the nucleotide epitope may be expressed in varying levels in a particular target cell type or ideotype.

FIG. 4 shows an antibody or antibody-like complex capable of blocking the pore (7) of a polymer pouch (6) containing a number of effector molecules (9) according to one embodiment. In certain embodiments, these antibodies or antibody-like complexes are held in the pores (7) by Fc-associated holder molecules (8). In some embodiments, this holder molecule may be Surface Protein A of Staphylococcus aureus. This blockage of the pore (7) may keep the effector molecules (8) from interacting with the cellular environment. The detection domain (2) of an embodiment may be specific for an epitope of interest, as those mentioned in previous embodiments. Binding of an epitope of interest induces conformational changes in the remainder of the complex, the activation domain (3). This dissociates the holder molecule (8), which in turn leaves the pore (7) free for effector molecules (9). The effector molecules (9) escape into the environment and interact, causing downstream effects. As in the previous embodiment, this could result in the death of the cell or some other downstream effect.

Figures 7, 8A:
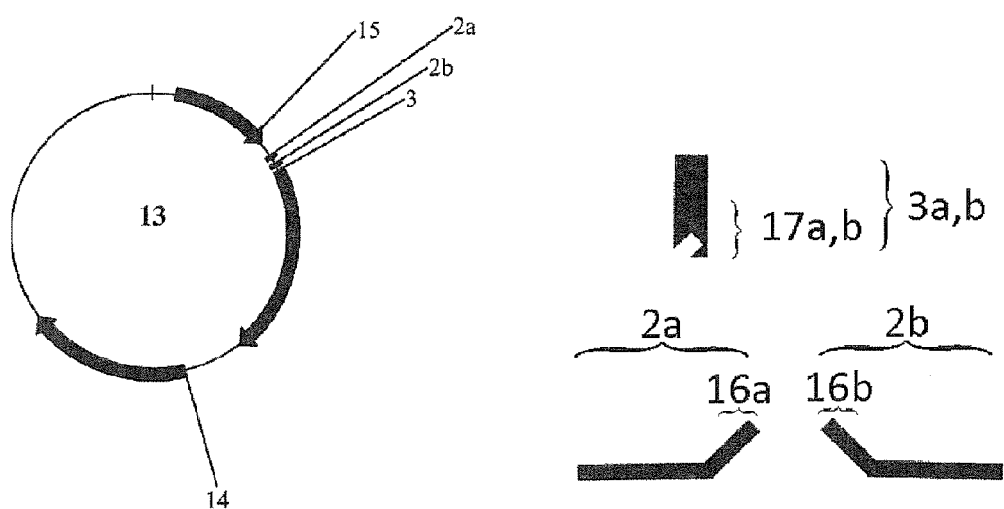
FIG. 7 shows an example plasmid construct of Ideotypically Modulated Pharmacoeffectors, giving instructions to target cells for the introduction of Ideotypically Modulated Pharmacoeffectors into the cell according to one embodiment.
FIG. 8A shows an example of the products of an example plasmid construct from FIG. 7.
Figure 8B:
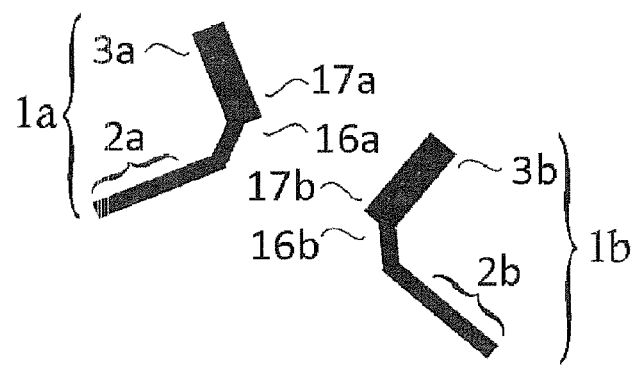
FIG. 8B shows an example of a self-assembled combination of parts shown in FIG. 8A.

FIG. 7 shows an example plasmid construct of Ideotypically Modulated Pharmacoeffectors (13), giving instructions to target cells for the introduction of Ideotypically Modulated Pharmacoeffectors into cells according to one embodiment. Various nucleotide sequences found on a plasmid (15) may, among other functions, promote the expression of nucleotide sequence detection domains (2a, 2b) and a protein activation domain (3). According to one embodiment shown in FIG. 8A, an activation domain (3a,3b) may comprise a fusion of a ribonucleoprotein subunit (17a,b) and a caspase. The terms "ribonucleoprotein" and "nucleoprotein" as used herein refer to any nucleotide-binding protein or protein subunit; they may be produced artificially or are found naturally (e.g. riboswitches). Such a fusion can be produced using widely-available recombinant gene techniques. A detection domain (2a,2b) may comprise a fusion of a ribonucleoprotein-binding specific ribonucleotide sequence (16a,16b) and a sequence that is complementary to a target sequence found in cells of interest. In one instance, a cell may be induced by a plasmid to introduce both detection and activation domains into the cell. Since an activation domain contains a subunit ribonucleoprotein (17a,b) that binds a ribonucleoprotein-specific ribonucleotide sequence (16a,b) found in a detection domain, an IMP may self-assemble as shown in FIG. 8B and function much like an embodiment described in FIG. 3C. Various uptake sequences (14) may be part of the plasmid to induce uptake into the cell. The term "uptake sequence" as used herein refers to sequences by which the cell is induced to import the plasmid into the cell.

The introduction of IMPs into a cell for the detection of intracellularly-expressed epitopes as may be required in some embodiments may be accomplished by a number of mechanisms. Modified viral vectors (with the embodiment in the place of nucleotide material) may offer cell-specific or generalized introduction of the embodiments into the cell. Such constructs have been developed for gene therapy and may be modified for this purpose. Rather than injecting nucleotide material to be inserted into the host genome, these constructs may contain IMPs. Other potential methods include receptor-mediated endocytosis, which is also used by cells and viruses alike to take in exogenous materials. In one instance, an IMP may have a subunit with affinity for a surface receptor on all or a subset of cells. As a result of binding, the IMP may be brought into the cell. In one instance, a plasmid may contain a sequence ("uptake sequence") that is recognized and taken up by some cells. As reference above, the term "uptake sequence" as used herein refers to sequences by which the cell is induced to import the plasmid into the cell. In some instances, an embodiment may be encapsulated in a colloid suspension, which may make the embodiment sufficiently amphiphilic to allow association with the lipid bilayer. Similarly, liposomes containing an IMP or IMPs may be coated with materials that may make them more likely to be taken up by a cell. For instance, an array of positive charges on a liposome containing an embodiment may allow non-specific cell bilayer association and fusion. The association of particular peptides may also help to encourage uptake of liposome contents. Different cellular compartments may require different delivery methods. These methods are only some of the ways in which the embodiment could be introduced into the cell and should not be considered limiting. Further, not all embodiments may need to be taken up into a cell to be effective. Further examples of cell entry mechanisms are described below with reference to FIGS. 2A-6.

A. Embodiments as May be Used in Viral Diseases

In various embodiments, viral diseases including but not limited to HIV may be treated. For instance, the use of an embodiment like those shown in FIGS. 1 and 2 may cause HIV-infected cells to die by apoptosis. The term "apoptosis" as used herein refers to programmed cell death in which the cell is induced by internal and/or external signaling to die. The term "apoptose" as used herein refers to the action of apoptosis of a cell. In one embodiment, the detection domain (2) of the Ideotypically Modulated Pharmacoeffectors (1) could be antibody fragments with specificity for adjacent epitopes (4) on HIV Reverse Transcriptase (HIV RT). HIV RT expresses epitopes that are unique and may not be found in normal, uninfected human cells. This may allow the differentiation of two ideotypes of cells: infected and uninfected. As previously described, the term "ideotype" as used herein refers to the uniqueness of the set of antigens expressed in or on a subset of cells. HIV RT is necessary for the virus to mount a successful cell invasion and will therefore be found in every HIV-infected cell. The activation domain (3) of an embodiment may be Fas-associated protein with death domain (FADD). When FADD trimerizes naturally in a cell in sufficient numbers, it causes the assembly of the death inducing signaling complexes (DISCs) that signal downstream to terminate the cell. Thus when three IMPs (1) bind adjacent epitopes (4) on HIV RT, the three FADD activation domains (3) may trimerize to cause downstream DISC formation. This may cause apoptosis of those cells in which sufficient DISCs are formed, which may be cells of the infected ideotype.

Another similar embodiment may be used in viral diseases. Detection domains (2a,2b) may comprise antisense nucleotide strands of RNA or DNA as shown in FIGS. 3A-C. In HIV infections, for instance, there are well-conserved RNA sequences that are introduced into the cell or produced by the cell as a result of the infection. A detection domain (2a,2b) of an embodiment may comprise antisense nucleotide strands that are complementary to adjacent conserved sequences of ideotypical viral nucleotides (4). These strands could be manufactured by using PCR or by transfecting bacteria to produce them. The activation domain (3a,3b) of an embodiment may be an inactive monomer of Caspase-9. When Caspase-9 dimerizes in nature, it becomes self-activating and causes cell apoptosis. A detection domain (2) and an activation domain (3*a*,3*b*) may be conjugated together through a benzaldehyde group interacting to an N-terminal histamine residue on the activation domain using a modified Pictet-Spengler reaction in glacial acetic acid. In this artificial embodiment, the binding of the anti-sense strands (2*a*,2*b*) to adjacent portions of an HIV-specific nucleotide strand (4) may bring the activation domains (3*a*,3*b*) into contact such that they may dimerize. The cell may apoptose when this occurs in sufficient numbers.

Another similar embodiment may be used in viral diseases. Detection domains (2*a*,2*b*) may comprise antisense nucleotide strands of RNA or DNA as shown in FIGS. 3A-C. In HIV infections, for instance, there are well-conserved RNA sequences that are introduced into the cell or produced by the cell as a result of the infection. A detection domain (2) and an activation domain (3*a*,3*b*) may be encoded for on a plasmid, as in one embodiment shown in FIG. 7. The plasmid may contain a sequence that enhances uptake into cells of interest. The plasmid may encode detection (2*a*,2*b*) and activation (3) domains as shown in FIG. 8A. In this artificial embodiment, an activation domain may comprise a fusion of a procaspase-9 subunit and a ribonucleoprotein subunit (17*a,b*). A detection domain may comprise a fusion of anti-sense nucleotide strands that recognize an HIV-specific nucleotide strand and a ribonucleoprotein-binding strand (16*a,b*) that is specific for the ribonucleoprotein subunit found in an activation domain. In this artificial embodiment, a cell containing a plasmid produces the domains, which self-assemble as shown in FIG. 8B by the interaction of a ribonucleoprotein-binding nucleotide portion (16*a,b*) of a detection domain with a ribonucleoprotein subunit portion (17*a,b*) of an activation domain. In this artificial embodiment, the binding of the anti-sense strands (2*a*,2*b*) to adjacent portions of an HIV-specific nucleotide strand (4) may bring the activation domains (3*a*,3*b*) into contact such that they may dimerize. The cell may apoptose when this occurs in sufficient numbers.

While existing treatments may also be used to combat viral diseases including HIV, Ideotypically Modulated Pharmacoeffectors (IMPs) offer a number of advantages over these treatments. First and foremost, various embodiments of the present disclosure may allow the termination of infected cells before escape variants can be produced by the virus. Since the epitopes detected by IMPs may be selected such that they are conserved, even widely-mutated strains of any given virus may still express them. Further, all of the viral strains in a given cell—even those which have mutations that might make them superior escape variants—may be destroyed when a cell apoptoses. This means that IMPs, unlike existing treatments, may not naturally select evolutionarily superior strains of a virus. This may further mean that IMPs may not cause nor be affected by resistance mechanisms developed by the virus. This is in direct contrast to presently-available antivirals and antibiotics. Another advantage of IMPs may be their scope of effectiveness. While most current antiviral medications only interfere with the growth of the virus, IMPs may clear an infection completely. This gives the further advantage that IMPs may be much more cost-effective than existing treatments, since IMPs may not necessitate long-term treatment. In addition, the complete clearance of disease may eliminate the risk for further transmission. Related to all of the above-mentioned advantages, IMPs may avoid the unpleasant side effects of other treatments. These may include lipodystrophy, liver toxicity, and inflammation, amongst others. These side-effects lead a large fraction of patients to forego treatment (e.g. 25% of patients undergoing HAART for HIV infections). Without these side-effects, IMPs may result in higher treatment compliance.

While the above examples describe IMPs that would target HIV epitopes, these and other embodiments may be adjusted for other viral diseases. This could include, for example, viruses that cause the common cold, Dengue fever, Epstein-Barr, HPV, Hantavirus, various forms of hepatitis, herpes, influenza, rotavirus, and others. Thus the present embodiment should not be limited to these examples. Nor are these the only embodiments of IMPs by which HIV may be combated. Various embodiments may also be used simultaneously (i.e. various detection domains and a variety of activation domains). This may give an advantage in that it may provide redundancy against potential resistance mechanisms.

B. Embodiments as May be Used in Other Infectious Intracellular Disease

Various embodiments of IMPs could also work against intracellular disease-causing organisms like bacteria or parasites. These disease-causing pathogens, including *Rickettsiae* and *Chlamydia* species, can pose problems similar to those of viruses. They also express unique epitopes that may not be found in normal, uninfected cells. As previously, cells can be categorized into ideotypes of infected and uninfected.

In a particular embodiment to treat a *Chlamydia* infection, there may be a detection domain (2) that is a lectin. Lectins are found in nature and are capable of binding specific sugars, as are frequently expressed on the surface of specific bacteria. Some lectins, for instance, are quite specific to the sugars expressed on species of *Chlamydia*. The activation domain (3) in this embodiment may include various antimicrobials. In one embodiment using the pouch-based embodiment shown in FIG. 4, the effector molecules (9) may include antimicrobials like peptidoglycan lyase. Peptidoglycan lyase is an enzyme that digests the protective barrier found on the surface of most bacteria. On binding of lectins (2) to the specific sugars found on an invading bacterial cell wall in ideotypical cells, peptidoglycan lyase would be freed to digest bacterial cell barriers.

While the above example describes an IMP using one embodiment against a *Chlamydia* infection, many different embodiments are possible for various intracellular pathogens. For instance, the activation domain could signal apoptosis in the cell and the death of the cell could also eliminate the intracellular pathogen.

C. Embodiments as May be Used in Treating Cancers

Various embodiments of IMPs could also be used to treat and/or prevent cancers. Malignant cells may be ideotypical in that they may express epitopes that are either unique or enriched to these cells. The term "malignant cell" or "cancerous cell" as used herein refers to any cell that proliferates out of control as a result of genetic and/or metabolic changes in the cell. These epitopes may vary in their expression levels and distribution depending on the situation. Some epitopes are expressed in all or most cancer types, while others are only present in few. Some epitopes may never be expressed in non-malignant cells, while others may only have elevated expression levels in malignant cells.

In a particular embodiment to eliminate cancerous cells, there may be a detection domain (2) that is an antibody fragment specific for a mutated form of the protein p53 (4) found in some cancers. An activation domain (3) may comprise inactive Caspase-9 monomer. In cells of the malignant ideotype, the detection domains (2) of multiple IMPs (1) may bind the mutated p53 (4). Their activation domains (3) may dimerize to cause downstream signaling in the cell. When this signaling reaches sufficient levels, the cell may apoptose.

In another embodiment to eliminate prostate cancer, a detection domain (2) may comprise an antibody fragment specific for PSA (prostate specific antigen). While PSA is ideotypical of all prostate cells rather than just cancerous cells, it may be more effective in coping with prostate cancer after it has been diagnosed. An activation domain (3) may comprise inactive Caspase-9 monomer. If administered in smaller amounts, the embodiment may lower the threshold of natural cellular self-killing. In cancerous cells, this may induce cell death at a lower level than in non-diseased cells.

In still another embodiment to eliminate Chronic Myelogenous Leukemia (CML), cancerous immature leukocytes proliferate out of control as a result of a translocation. This translocation creates a fusion of the breakpoint cluster region and Abl1, resulting in unregulated growth. Detection domains (2a,2b) similar to the embodiment in FIG. 1 may be antibody FAb fragments against part of the Abl1 protein and part of the breakpoint cluster region protein (4). Detection domains (2a,2b) similar to the embodiment in FIG. 3C may comprise specific nucleotide sequences against part of the Abl1 nucleotide sequence and part of the breakpoint cluster region nucleotide sequence. Activation domains (3a,3b) may comprise inactive Caspase-9 monomers. In Ideotypical CML cells (i.e. those that express the fusion protein), the two different detection domains (2a,2b) may bind to bring two activation domains (3a,3b) together. These activation domains may interact, causing cell death. This may eliminate cancerous cells.

In still another embodiment, detection domains (2a,2b) may comprise antisense nucleotide strands of RNA or DNA as shown in FIGS. 3A-C. In CML, for instance, there are well-conserved sequences that are produced by the cell as part of the cancer. A detection domain (2) and an activation domain (3a,3b) may be encoded for on a plasmid, as in one embodiment shown in FIG. 7. The plasmid may contain a sequence that enhances uptake into cells of interest. The plasmid may encode detection (2a,2b) and activation (3) domains as shown in FIG. 8A. In this artificial embodiment, an activation domain may comprise a fusion of a ribonucleoprotein subunit (17a,b) and a procaspase-9 subunit. A detection domain may comprise a fusion of a ribonucleoprotein-binding strand (16a,b) that is specific for the ribonucleoprotein subunit found in an activation domain and anti-sense nucleotide strand or strands that recognize nucleotide sequences produced by the cell as part of the cancer. In this artificial embodiment, a cell containing a plasmid produces the domains, which self-assemble as shown in FIG. 8B by the interaction of a ribonucleoprotein-binding nucleotide portion (16a,b) of a detection domain with a ribonucleoprotein subunit portion (17a,b) of an activation domain. In this artificial embodiment, the binding of the anti-sense strands (2a,2b) to adjacent portions of a nucleotide strand (4) may bring the activation domains (3a,3b) into contact such that they may dimerize. The cell may apoptose when this occurs in sufficient numbers.

In treating cancers, IMPs may have the distinct advantage that they may only substantially affect targeted ideotypical cancer cells. This may spare non-malignant cells from the effects of treatment. Current cancer treatments often employ drugs that disrupt cell growth, but this disruption causes severe collateral damage and side-effects. By sparing non-malignant cells, IMPs may avert the substantial side-effects of chemotherapeutics and radiation therapies. Further, chemotherapeutics and radiation therapies take a shotgun approach to proliferating cells. Newer therapies and the human immune system do attempt to create a more targeted response by recognizing such cells externally, but cancerous cells mutate rapidly and their surface antigens are often hidden. IMPS, on the other hand, may target all rather than just a subset of cancerous cells by recognizing epitopes inside the cell that are less likely to be hidden or mutable. This improved combination of specificity and efficacy of treatment may result in complete eradication of cancers in some patients.

While the above example describes IMPs using embodiments against particular cancer-associated antigens, many different embodiments are possible for various cancers and patient types. Further, aberrant nucleotide strands or other metabolites may provide similarly efficacious epitopes to be detected. These examples above should not be construed as limiting other embodiments that target cancers.

D. Embodiments as May be Used in Treating Extracellular Bacterial Infections

Various embodiments of IMPs may also be used to treat extracellular infections. As with antivirals, existing treatments for bacterial diseases (i.e. antibiotics) favor natural selection of pathogens that evolve resistance mechanisms. Antibiotic resistance is a common problem, especially in environments like hospitals where antibiotics and multiple disease-causing organisms are frequently brought into contact. A related problem with antibiotics is their non-specificity against virulent bacteria. The term "virulent" as used herein refers to the state of any resident organism in which the organism expresses genes that help it to cause disease in a host organism. Most bacteria found in and on human beings are not virulent and are sometimes called "avirulent" strains. Unfortunately, antibiotics commonly target both virulent and avirulent organisms. Further, many virulent strains—including XDR. Tuberculosis and MRSA—are those which have developed the strongest resistance mechanisms to existing antibiotics. Thus treating an individual with antibiotics may actually help the virulent strains to spread by removing avirulent strains that are competing for the same resources.

To further complicate matters, any given bacterium can switch from being avirulent to being virulent by expressing virulence genes. The terms "virulence genes" and "virulence factors" as used herein refer to the genes and gene products of a resident organism that help it to cause disease in a host organism. Virulence factors may include various toxins, adhesion molecules (invasins), secretion system proteins, enzymes, capsule proteins, and immunosuppressants, to name a few. Not all strains of bacteria in a given species express or even possess virulence genes at any given time. However, all organisms that are virulent at any given time express some virulence genes. The expression of mRNA and protein from these virulence genes in high levels may be unique to virulent cells, making them ideotypical. It should be noted that these particular ideotypical cells are not human, but rather are bacterial cells.

In a particular embodiment of IMPs (1a,2b) targeting virulent Staphylococcus aureus, detection domains (2a,2b) could comprise an antibody fragment that is specific for alpha-hemolysin or Hla (4). Hla is an especially potent toxin expressed only in virulent *Staph aureus* and not in avirulent strains of the same bacterium. An activation domain (3) could comprise a monomer of an antibacterial toxin that is effective only as a dimer. If adjacent epitopes on alpha-hemolysin are detected by the detection domains (2a,2b) inside *Staph* cells of the virulent ideotype, the activation domains (3a,3b) may be brought into contact and dimerize. This may cause the death of virulent bacteria but spare avirulent strains and species.

The embodiment above and other embodiments of IMPs may have a number of advantages over existing antibiotics. First, IMPs may circumvent the resistance mechanisms of currently-resistant bacteria. Second, in potentially-virulent strains IMPs may help naturally select variant strains that do not express virulence factors. This means that the evolutionary pressure exerted by IMPs may exactly oppose that of classical antibiotics. Classical antibiotics select for strains that can express virulence genes that directly inactivate the antibiotics, whereas IMPs may select for strains that avoid expressing virulence factors altogether. Third, IMPs may not affect avirulent commensal organisms. This means that patients using IMPs may not be susceptible to other infections as they would be when taking antibiotics. IMPs may actually give avirulent commensal organisms an evolutionary advantage over virulent organisms, keeping the patient's balance of bacterial flora in a favorable equilibrium.

E. Embodiments as May be Used in Eradicating Vector-Borne Parasites

Various embodiments of IMPs could also be used to treat vector-borne parasites. The term "vector-born parasites" as used herein refers to parasitic organisms that are transferred to humans and/or to other animals by a "vector" organism like a mosquito, a tick, or some other intermediary. These parasites can include bacteria, fungi, yeasts, and protozoa. These diseases present a particular problem in that there are often vast reservoirs of infection. The term "reservoir" as used herein refers to animals other than humans in which a parasitic organism can grow and multiply and eventually be transferred by a vector to other animals or to humans. A reservoir may or may not experience a disease state from the parasite. Examples of such parasites and their diseases include sleeping sickness and Chagas disease (caused by trypanosomes from tsetse flies and assassin bugs, respectively), Lyme disease (caused by *Borrelia burgdorferi* from ticks), and Tularemia (caused by *Francisella tularensis* from various arthropods), to name a few.

Vector abatement programs have been used against such parasites, notably the malaria-causing protozoan parasite *Plasmodium falciparum*. The mosquitoes that carry malaria have been the target of such programs in which chemicals are used to deplete the population of potential carriers. Unfortunately, this has not eradicated the disease. First, killing all mosquitoes of a given species would be very difficult. Second, even killing the vast majority of mosquitoes of a given species would have unexpected and potentially-hazardous environmental consequences because of the ecological niche that the mosquitoes fill. The killing of reservoir animals from which vectors pick up the disease could have similarly dire consequences.

In one particular embodiment of IMPs, malaria-carrying mosquitoes may be targeted. Note here that an entire organism—a mosquito—can be grouped into two designated ideotypes: carrier and non-carrier. A detection domain (2) may comprise an antibody fragment specific for var gene products that are expressed copiously on the surface of the protozoa. An activation domain (3a,3b) may comprise an inactive subunit of an arthropod-specific toxin. In this embodiment, heterodimerization or heteromultimerization may produce an active toxin. Such an embodiment may be introduced to mosquitoes by injecting it into a species that the vector mosquitoes generally feed on. As the mosquito ingests the blood of the animal, it also ingests the IMPs (1). It may also be introduced by providing it in available water sources. In mosquitoes that are not colonized by Plasmodium (i.e. non-carrier ideotype), the IMPs (1) have no epitopes (4) to bind and may therefore be inert. In carrier mosquitoes, however, the activation domains (3*a*,3*b*) may dimerize or multimerize to form the full toxin. In the presence of sufficient toxin, the carrier mosquito may die.

A similar embodiment to target malaria-carrying mosquitoes may have the same detection domain (2) but have activation domains (3*a*,3*b*) on different IMPs comprised of either a pro-toxin or a weakened enzyme to convert the toxin into its active form. As the detection domains (2) of two different IMPs (1*a*,1*b*) bind to adjacent epitopes (4), the pro-toxin (3*a*) and weak enzyme (3*b*) interact as may not be possible in solution because of the enzyme's relative non-specificity. Once the pro-toxin is converted in sufficient amounts, the carrier may die.

The embodiment above and other embodiments of IMPs against carriers of vector-borne parasites may have a number of advantages. IMPs may target only those vectors that are actually of the carrier ideotype. Since this may be just a fraction of the vector population, it may allow the ecological niche that would be vacated by expired carriers to be filled seamlessly by non-carriers of the same species. This may minimize the environmental impact of the treatment. Further, IMPs in this example may promote the natural selection of vectors of any given species that are themselves resistant to colonization by the parasite. In some diseases, species that are resistant to colonization have already been described. These populations may be enriched in areas where carriers are selected against because of the added evolutionary advantage. The end goal of these treatments may be to eliminate transmission to human hosts. By cutting off the vector source of the parasite, the parasite may no longer be transmitted. Without such transmission, the disease may be eradicated entirely from a single region or from the world at large. Additionally, all this may be accomplished without immunization of the human population.

The above example is illustrative of the use of IMPs against vector-borne malaria. However, many other embodiments of IMPs targeting various parasitic diseases in various ways are possible. Further, other embodiments may be used to target malaria. For example, an embodiment may be introduced to the potential-carrier vector population by various other means including by directly feeding the vector a solution containing IMPs. These feedings may be protected such that a feeding station may not itself become colonized by the parasite. Thus the above examples should not be considered limiting.

F. Embodiments as May be Used in Autoimmune Disorders

Various embodiments of IMPs could also be used to treat a variety of autoimmune disorders. The terms "autoimmune disorder," "autoimmune disease," or "autoimmune syndrome" as used herein refer to any disease in which the human immune system causes or exacerbates the disease. This may include classical autoimmune disorders like Systemic Lupus Erythematosus (SLE), Rheumatoid Arthritis (RA), and Type I Diabetes as well as immunoproliferative disorders (cancers involving immune cells), transplant scenarios, allergies, and infectious diseases in which primary harm is caused by the immune system.

B and T cells of the immune system are both major and unique cells in the human body. They express a wide variety of receptors called antigen receptors, which bind various antigens throughout the body. The term "antigen receptor" as used herein refers to receptors on the B cell that are also often referred to as the B cell receptor (BCR), membrane-bound Ig (mIg), and antibodies (Ab) as well as to receptors on the T cell that are also referred to as the T cell receptor (TCR). Each clonal population of B or T cells only expresses one antigen receptor that is specific to a particular antigen. The term "clonal" as used herein refers to a group of cells that come from the same parent B or T cell. Clonal cells may be cells of a single ideotype, meaning cells that express similar epitopes (e.g. the antigen receptor).

FIG. 5 shows a detection domain (2) linked to an activation domain (3) by a linker (10) according to one embodiment. A detection domain (2) may be an antigen for which a clonal (and ideotypical) subpopulation of cells expresses a particular antigen receptor. An activation domain (3) may be FasL. FasL is a molecule that, when trimerized, may interact with the receptor Fas on the surface of nucleated cells to induce downstream signals that cause the death of the cell.

FIG. 6 shows the binding of a plurality of Ideotypically Modulated Pharmacoeffectors (1) to the surface antigen receptors (4) of ideotypical disease-causing B cells (11) according to one embodiment. As in FIG. 5, a detection domain (2) may be an antigen for which a clonal, ideotypical subpopulation of cells expresses a particular antigen receptor and an activation domain (3) may be FasL. The detection domains (2) may bind the antigen receptors (4) of the disease-causing cells (11). When a plurality of Ideotypically Modulated Pharmacoeffectors binds, the FasL activation domains (3) trimerize. When FasL has trimerized, it may interact with the receptor Fas (12) on the surface of the cells to induce downstream signals. These downstream signals may cause the death of the cell.

In a particular IMP embodiment to treat an immunoproliferative disorder like Burkitt's lymphoma, the malignant B or T cell population is derived from a single cell. This means that the malignant cell population is clonal and each of these cells expresses the same or closely-related antigen receptor (i.e. has the same ideotype). The embodiment's detection domain (2) may be an antigen for which the antigen receptors (4) of cancerous cells are specific. In the case of an immunoproliferative disorder, an ELISA screen of potential antigens may elucidate which antigen this should be. The embodiment's activation domain (3) may be FasL, which is a ligand that—when trimerized—may interact with the Fas receptor found on all nucleated cells' surfaces. The targeted antigen receptors (4) may interact with IMPs on ideotypical disease-causing cells through the detection domain (2). This may bring a plurality of activation domains (3) into close proximity and they may trimerize. As a result of this trimerization, these activation domains may interact with the Fas receptor (12) on the surface of said cells to cause downstream signaling that induces apoptosis in the cell. The death of these cells may clear the disease.

With reference to the previous embodiment and several embodiments that follow, if the embodiment is against a B cell malignancy, an antibody (antigen receptor) on the surface of said B cells may actually provide the epitopes (4) to which the detection domains (2) bind. On the other hand, in other embodiments previously listed an antibody may be part of the embodiment's detection domain. In this example, however, the detection domain (2) may comprise the antigen for which said antigen receptors (4) are specific. In an embodiment against a B cell malignancy, the detection domain (2) may also comprise an antibody that is specific for the membrane-bound antibody. Other IMP embodiments may be used to treat patients with classical autoimmune disorders like Systemic Lupus Erythematosus (SLE). Classically-defined autoimmune diseases generally follow a pattern of mistakes in the screening of B and T cells that are reactive to self antigens. The term "self antigen" as used herein refers to proteins and other metabolites produced by the human body. When B and T cells are reactive to self antigens, such cells are termed "autoreactive." When these cells escape the screening processes of the body, they can cause damage and interrupt important processes in the body. In patients with SLE, for instance, disease-related B and T cells are autoreactive to nuclear antigens. The detection domain (2) of an embodiment may comprise such nuclear antigens. These could be determined by ELISA. The activation domain (3) of an embodiment may comprise FasL as in some previous embodiments. Once introduced into the blood stream or lymph, a plurality of IMPs (1) would bind the antigen receptors (4) of the autoreactive cell ideotype (11). This would bring the activation domains (3) of multiple IMPs (1) together to trimerize. Trimerized activation domains (3) may interact with the Fas receptor (12) on said cells, inducing apoptosis of the cell. Since the epitope (i.e. antigen receptor specific for the detection domain) may not be present on the surface of cells that do not contribute to disease, these cells may be spared. In some autoimmune disorders, multiple ideotypes may be present and may be targeted with separate embodiments.

The T cell antigen receptors (TCRs) differ from B cell receptors (BCRs) in that they recognize an antigen in the context of an MHC molecule on other cells. In targeting autoreactive T cells, therefore, some adjustment in the detection domain may be necessary to accommodate this difference. This may include adding an MHC motif to the detection domain (2).

In still another embodiment for treatment of autoimmune disorders, detection domains (2a,2b) may comprise antisense nucleotide strands of RNA or DNA as shown in FIGS. 3A-C that are specific for sequences found in autoimmune B and/or T cells. Autoimmune B and T cells have unique nucleotide sequences as a result of viral changes or somatic recombination. The term "somatic recombination" as used herein refers to the V(D)J recombination that takes place during B and T cell receptor maturation. These unique sequences are an ideotypic change that could be exploited using IMPs with complementary nucleotide strands. The determination of these sequences for any given ideotype of autoimmune B or T cells could be accomplished using simple and well-understood techniques such as gene sequencing and subtractive hybridization. Such cells may be extracted from a patient or from cell culture for these studies. A detection domain could be simply reverse-engineered from these unique sequences. A detection domain (2) and an activation domain (3a,3b) may be encoded for on a plasmid, as in one embodiment shown in FIG. 7. The plasmid may contain a sequence that enhances uptake into cells of interest. The plasmid may encode detection (2a,2b) and activation (3) domains as shown in FIG. 8A. In this artificial embodiment, an activation domain may comprise a fusion of a ribonucleoprotein subunit (17a,b) and a procaspase-9 subunit. A detection domain may comprise a fusion of a ribonucleoprotein-binding strand (16a,b) that is specific for the ribonucleoprotein subunit found in an activation domain and anti-sense nucleotide strand or strands that recognize nucleotide sequences as discussed above in the target cells. In this artificial embodiment, a cell containing a plasmid produces the domains, which self-assemble as shown in FIG. 8B by the interaction of a ribonucleoprotein-binding nucleotide portion (16a,b) of a detection domain with a ribonucleoprotein subunit portion (17a,b) of an activation domain. In this artificial embodiment, the binding of the anti-sense strands (2a,2b) to adjacent portions of a nucleotide strand (4) may bring the activation domains (3a,3b) into contact such that they may dimerize. The cell may apoptose when this occurs in sufficient numbers. Other IMP embodiments may be used to combat allergies. The terms "allergy" and "allergies" as used herein refer to immune responses against otherwise-innocuous foreign antigens. The term "foreign antigens" refers to metabolites (e.g. proteins, lipids, carbohydrates) that were not produced by the body. Innocuous foreign antigens are often found in the body and should not normally cause an immune response. B cells producing a certain class of antibody against these antigens are a major part of many of these hypersensitivities. Like a previously-mentioned embodiment, an embodiment for the purpose of clearing B cells of the allergy-causing ideotype may have a detection domain (2) that is the foreign antigen. The activation domain (3), as previously, may be FasL. As before, the detection domains (2) may only bind the antigen receptors (i.e. epitopes) of ideotypical disease-causing cells (11). The activation domains (3) may trimerize and interact with the Fas receptors (12) on the cell surface, causing apoptosis.

Other IMP embodiments may further be used to combat graft-versus-host disease (GVHD). In GVHD, transplanted tissues retain their immunogenicity in the new host and cause damage to the host's existing tissues. This is generally considered the opposite of transplant rejection, wherein the transplant actually rejects the host. Donor tissue's natural killer and NK T cells, which have specific antigen receptors called KIRs for donor cells' unique MHC molecules, fail to recognize the new host tissue and therefore determine that it is foreign. This leads to the "rejection" of the host by the donor tissue, and an immune response is mounted against the host. In one embodiment, the detection domain (2) may be the donor cells' MHC molecules. The activation domain (3) may be FasL. As in the previous examples, Ideotypically Modulated Pharmacoeffectors (1) may bind the antigen receptors of disease-causing (NK and NK T) cells (11). The activation domains (3) may in turn trimerize and signal death through the Fas receptor (12). This may clear the donor tissue of unwanted immune cells and may avert GVHD.

On the other hand, other IMP embodiments may also be used to combat transplant rejection. Transplant rejection is the rejection of donor tissue by the host, which is handled by at least two ideotypical sets of host cells. One subset is host T cells with antigen receptors (TCRs) that recognize the unique MHC of the donor tissue. Another subset is host B cells that produce anti-donor-MHC antibodies. These antibodies are a common cause of long waits on donor waiting lists for patients receiving transplants after a previous rejection. When the MHC of the donor tissue does not match the MHC of the host, these cells induce death in donor cells. An IMP embodiment to combat transplant rejection may have a detection domain (2) that is a mimetic of the donor's MHC molecules. An activation domain (3) may be FasL. The detection domain (2) may bind the antigen receptors (4), whether TCRs or BCRs, of host T and B cells. The activation domains (3) may trimerize and interact with Fas receptors (12) on the offending T and B cells (11). This may signal cell apoptosis. If these subsets of host cells are ablated, a graft rejection may be avoided.

It should be noted that, in any of the above embodiments or other embodiments dealing with antigen receptors, soluble B cell receptors (i.e. secreted antibodies) may need to be cleared prior to treatment by plasmapheresis or some other method in order to give an embodiment clear access to the membrane-bound receptors.

In still another embodiment for treatment or prevention of graft-related morbidity, detection domains (2a,2b) may comprise antisense nucleotide strands of RNA or DNA as shown in FIGS. 3A-C that are specific for sequences found in rejecting B and/or T cells. Rejecting B and T cells have unique nucleotide sequences as a result of viral changes or somatic recombination. The term "somatic recombination" as used herein refers to the V(D)J recombination that takes place during B and T cell receptor maturation. These unique sequences are an ideotypic change that could be exploited using IMPs with complementary nucleotide strands. The determination of these sequences for any given ideotype of rejecting B or T cells could be accomplished using simple and well-understood techniques such as gene sequencing and subtractive hybridization. Such cells may be extracted from a patient or from cell culture for these studies. A detection domain could be simply reverse-engineered from these unique sequences. A detection domain (2) and an activation domain (3a,3b) may be encoded for on a plasmid, as in one embodiment shown in FIG. 7. The plasmid may contain a sequence that enhances uptake into cells of interest. The plasmid may encode detection (2a,2b) and activation (3) domains as shown in FIG. 8A. In this artificial embodiment, an activation domain may comprise a fusion of a ribonucleoprotein subunit (17a,b) and a procaspase-9 subunit. A detection domain may comprise a fusion of a ribonucleoprotein-binding strand (16a,b) that is specific for the ribonucleoprotein subunit found in an activation domain and anti-sense nucleotide strand or strands that recognize nucleotide sequences as discussed above in the target cells. In this artificial embodiment, a cell containing a plasmid produces the domains, which self-assemble as shown in FIG. 8B by the interaction of a ribonucleoprotein-binding nucleotide portion (16a,b) of a detection domain with a ribonucleoprotein subunit portion (17a,b) of an activation domain. In this artificial embodiment, the binding of the anti-sense strands (2a,2b) to adjacent portions of a nucleotide strand (4) may bring the activation domains (3a,3b) into contact such that they may dimerize. The cell may apoptose when this occurs in sufficient numbers.

The previous examples of embodiments for various autoimmune disorders should not be construed as limiting. Different detection domain (2) and activation domain (3) combinations may be used and different embodiments and applications are possible. Each of these example embodiments and other embodiments not listed here may offer a number of advantages, mostly having to do with treatment specificity and efficacy. In the case of immunoproliferative disorders, IMP embodiments may clear the malignancy and restore the patient to normal status without the side-effects of chemotherapeutic and radiation therapy methods. In the case of autoimmune disorders, embodiments may clear the offending autoreactive B and/or T cells at the center of the disorder, either ameliorating symptoms or curing the disease. In the case of the twin diseases of GVHD and transplant rejection, these combined embodiments may increase the likelihood of transplant success. All this may be accomplished without the immunosuppression that is a common feature of most treatments for this group of diseases. This may be especially important because many of these patients are already immunocompromised.

G. Embodiments as May be Used in Ameliorating Cellular Disease and/or Enhancing Cellular Function In some cellular diseases, certain subsets of cells fail. These cells may have a given task, like providing structural strength to surrounding tissue or providing an important hormone or metabolite to other parts of the body. A number of embodiments may induce the production of metabolites in such cells to improve their function. For instance, muscular atrophy occurs in a number of diseases. One embodiment may have a detection domain (2) for troponin (4), a metabolite produced in large quantities in muscle cells. An activation domain (3) may be subunits of an enzyme to help assemble actin subunits, adding strength to said muscle when the activation domains are brought together.

Some embodiments may be effective in patients with Type II Diabetes. In this form of diabetes, pancreatic beta cells producing insulin are overwhelmed with the production demands incurred by high sugar and lipid levels in the blood. An IMP may help by encouraging these ideotypical pancreatic beta cells or their stem cell progenitors to proliferate, or perhaps by increasing the anti-apoptotic pathways in existing beta cells. These IMPs may extend the life of these cells and may avert or postpone the onset of serious complications of disease.

Adipose cells may also offer a good target for some embodiments to combat lipodystrophic disease. In such diseases, adipose cells are unable to handle the volume of fats in the bloodstream. This leads to disease. By interacting with such cells specifically, their capacity may be adjusted or their survival pathways may be bolstered. Activation domains (3) of some IMP embodiments may interact with cellular pathways to decrease the efficiency of energy expenditure in the cell, depleting excessive energy stores.

Some current treatments for cellular diseases have non-optimal success rates as a result of collateral cell damage, especially amongst a certain subset of cells. Some embodiments may help ameliorate these side-effects in conjunction with other treatments by bolstering particular cell subsets (i.e. neurons, muscle cells, etc) from the effects of treatment. The previous examples of embodiments for various cellular applications should not be construed as limiting. Each of these example embodiments and other embodiments not listed here may offer a number of advantages, mostly having to do with treatment specificity and efficacy.

H. Embodiments as May be Used in Research Applications

Various embodiments of IMPs could be used in research applications. For instance, one embodiment may have a detection domain that is specific for proteins involved in cell differentiation. An activation domain (3) may be an inactive monomer of a fluorescence protein. The embodiment may be introduced to a cell tissue culture. When the protein (4) is present in any given cell, the detection domain (2) may bind it. Adjacent activation domains may dimerize to form an active fluorescent dimer, allowing visualization of the location and concentration of proteins in the cell as well as visualization of the cells expressing the protein.

Another embodiment may have a detection domain for mRNAs encoding certain proteins. A detection domain (2) may be an antisense nucleotide strand against the mRNAs (4). An activation domain (3) may be inactive subunits of an enzyme that cleaves mRNAs. In this case, when the mRNAs are produced in the cell, the detection domains may bind to adjacent RNA sequences. This may bring the subunits together, which may go on to cleave mRNA and limit its expression in the cell.

The above examples are illustrative of just a few of the ways in which IMPs could be used in a laboratory setting. Many other embodiments may exist for various other potential applications in research.

I. Embodiments as May be Used in Emerging or Weaponized Diseases

Various embodiments of IMPs could be used in combating emerging or weaponized diseases. For instance, various outbreaks of viral diseases have emerged as a result of human encroachment on previously-unsettled territories. Relatedly, various terrorist organizations have expressed interest and/or competence in mutating existing agents for the purpose of weaponization and attacks on urban populations.

While existing tools may also be used to combat emerging and weaponized diseases, Ideotypically Modulated Pharmacoeffectors (IMPs) offer important advantages over these treatments. For instance, the rapid mutation of emerging diseases and the artificial mutation of weaponized diseases make the production of new treatments difficult to achieve using currently-available methods. Using certain embodiments of IMPs, however, individuals combating these diseases could utilize the easily-altered specificity of detection domains in order to adapt one IMP embodiment for use against a changing threat. These embodiments could further be rapidly produced for use in emergency situations and adjusted as needed.

As an example embodiment for treatment of a viral agent that has been weaponized and mutated by a militant entity, an embodiment as shown in FIG. 7 may comprise a plasmid encoding various domains. Detection domains (2a,2b) may comprise antisense nucleotides as shown in FIGS. 3A-C that are specific for the target weaponized virus. The determination of these sequences for any given ideotype of weaponized virus could be accomplished using simple and well-understood techniques such as gene sequencing and subtractive hybridization. Such cells may be extracted from a patient or from cell culture for these studies. A detection domain could be simply reverse-engineered from these unique sequences. A detection domain (2) and an activation domain (3a,3b) may be encoded for on a plasmid, as in one embodiment shown in FIG. 7. The plasmid may contain a sequence that enhances uptake into cells of interest. The plasmid may encode detection (2a,2b) and activation (3) domains as shown in FIG. 8A. In this artificial embodiment, an activation domain may comprise a fusion of a ribonucleoprotein subunit (17a,b) and a procaspase-9 subunit. A detection domain may comprise a fusion of a ribonucleoprotein-binding strand (16a,b) that is specific for the ribonucleoprotein subunit found in an activation domain and anti-sense nucleotide strand or strands that recognize nucleotide sequences as discussed above in the target cells. In this artificial embodiment, a cell containing a plasmid produces the domains, which self-assemble as shown in FIG. 8B by the interaction of a ribonucleoprotein-binding nucleotide portion (16a,b) of a detection domain with a ribonucleoprotein subunit portion (17a,b) of an activation domain. In this artificial embodiment, the binding of the anti-sense strands (2a,2b) to adjacent portions of a nucleotide strand (4) may bring the activation domains (3a,3b) into contact such that they may dimerize. The cell may apoptose when this occurs in sufficient numbers. In the event of a mutation that would cause resistance of the target organism to any particular embodiment of IMPs, adjustments in detection domains may be easily undertaken using simple techniques to circumvent the resistance.

J. Summary of Example Embodiments

Although the above descriptions include a number of specific applications, these should not be considered limiting. Various techniques may be used in different contexts, and various contexts may benefit from different techniques and embodiments. For example, while a pouch-based embodiment in FIG. 4 has been mentioned in an example of an embodiment that may help treat a *Chlamydia* infection, a pouch-based embodiment may also be employed against ideotypical carrier vectors of a disease like malaria. Similarly, while an embodiment with a nucleotide sequence for a detection domain (2) has been mentioned in an example of an embodiment that may help treat an HIV infection, an embodiment with a nucleotide sequence detection domain (2) may be used in treating a cancer with characteristic or enriched nucleotide sequences (4) in the cell. Thus a number of variations may be applied without departing from the scope of the present disclosure. In addition, not all applications are part of the embodiments presented here. Thus the scope of the invention should be evaluated according to the appended claims.

It will be understood that well known processes have not been described in detail and have been omitted for brevity. Although specific steps, structures and materials may have been described, the present disclosure may not limited to these specifics, and others may substituted as is well understood by those skilled in the art, and various steps may not necessarily be performed in the sequences shown.

As just one example, the introduction of IMPs into a population of cells may be intra-body. For example, in particular embodiments, instructions for manufacturing IMPs may initially be introduced into a body. Then, when such IMPs are produced by cells within the body, the IMPs may be introduced to a population of cells within the body. Alternatively, the IMPs may be produced external of a body and introduced into the body. For example, the IMPs may be introducing into a population of cultured cells.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system for ideotype-specific treatments, the system comprising:
    a plurality of engineered, nonnaturally occurring Ideotypically Modulated Pharmacoeffectors (IMPs), each IMP comprising:
        a detection domain that has affinity for an epitope, wherein the detection domain binds single-stranded nucleotide sequences, and
        an activation domain coupled to the detection domain, the activation domain configured when activated to cause a downstream effect in a population of cells.

2. The system of claim 1, further comprising a linker molecule that conjugates the detection domain and the activation domain.

3. The system of claim 1, wherein the detection domain of each IMP comprises an antibody fragment.

4. The system of claim 1, wherein the detection domain of each IMP comprises a nucleotide sequence.

5. The system of claim 1, wherein the detection domain of each IMP comprises an antigen against which antigen receptors of a clonal subpopulation of cells are specific.

6. The system of claim 1, wherein the activation domain of each IMP comprises inactive Caspase-9 monomer.

7. The system of claim 1, wherein the activation domain of each IMP comprises a subunit of a bioactive molecule.

8. The system of claim 1, wherein the activation domain of each IMP comprises either a pro-toxin or a toxin-converting enzyme.

9. The system of claim 1, wherein the activating of the activation domain comprises binding a subset of the plurality of IMPs to adjacent epitopes, the binding of the subset of the plurality of IMPs causing the activation domains of the subset of the plurality of IMPs to interact with each other.

10. A system for ideotype-specific treatments, the system comprising:
    instructions for the manufacture of a plurality of Ideotypically Modulated Pharmacoeffectors (IMPs), each of the plurality of manufactured IMPs comprising:
        a detection domain that has affinity for an epitope, wherein the detection domain binds single-stranded nucleotide sequences, and
        an activation domain coupled to the detection domain;
    wherein the detection domain of each IMP of a subset of the plurality of manufactured IMPs is configured to bind to one or more epitopes; and
    wherein the activation domain of each IMP of the subset of the plurality of manufactured IMPs is configured to activate and cause a downstream effect in a population of cells.

11. The system of claim 10, wherein the instructions are encoded on a plasmid.

12. The system of claim 10, wherein detection domain(s) and activation domain(s) self-assemble to produce functional IMPs.

13. The system of claim 10, wherein self-assembly of IMPs is accomplished by affinity of a ribonucleoprotein subunit to a specific nucleotide sequence.

14. The system of claim 10, wherein the activating of the activation domain comprises binding a subset of the plurality of IMPs to adjacent epitopes, the binding of the subset of the plurality of IMPs causing the activation domains of the subset of the plurality of IMPs to interact with each other.

15. The system of claim 10, wherein the detection domain may be altered in its affinity such that the produced IMP becomes employable against a mutated target.

* * * * *